US00PP34897P2

(12) United States Plant Patent
Ren

(10) Patent No.: US PP34,897 P2
(45) Date of Patent: Jan. 3, 2023

(54) ***ECHINACEA* PLANT NAMED 'BALSOMPRED'**

(50) Latin Name: ***Echinacea* x *hybrida***
Varietal Denomination: Balsompred

(71) Applicant: Ball Horticultural Company, West Chicago, IL (US)

(72) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/948,316

(22) Filed: Sep. 20, 2022

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428, 226
CPC ... A01H 5/02; A01H 5/00; A01H 6/14; A01H 6/1448
See application file for complete search history.

(56) References Cited

U.S. PATENT DOCUMENTS

PP23,097 P2 * 10/2012 Ren ..... A01H 5/02 Plt./428

* cited by examiner

*Primary Examiner* — June Hwu
(74) *Attorney, Agent, or Firm* — Audrey Charles

(57) ABSTRACT

A new and distinct cultivar of *Echinacea* plant named 'Balsompred', characterized by its single-type, bright red-colored inflorescences, dark green-colored foliage, and moderately vigorous, compact-upright growth habit, is disclosed.

1 Drawing Sheet

Latin name of genus and species of plant claimed: *Echinacea* x *hybrida*.

Variety denomination: 'Balsompred'.

BACKGROUND OF THE INVENTION

The present invention relates to a new and distinct cultivar of *Echinacea* plant botanically known as *Echinacea* x *hybrida* and hereinafter referred to by the cultivar name 'Balsompred'.

The new cultivar originated in a controlled breeding program in Elburn, Ill. during July 2014. The objective of the breeding program was the development of *Echinacea* cultivars with a single inflorescence form having imbricate ray florets and a well-branched, compact-upright growth habit.

The new *Echinacea* cultivar is the result of cross-pollination. The female (seed) parent of the new cultivar is the proprietary *Echinacea* x *hybrida* breeding selection coded E101-4-10-C, not patented, characterized by its single-type, medium red-colored inflorescences, medium green-colored foliage, and moderately vigorous, semi-upright growth habit. The male (pollen) parent of the new cultivar is the proprietary *Echinacea* x *hybrida* breeding selection coded E68-7-3-3-2, not patented, characterized by its single-type, dark orange-colored inflorescences, medium green-colored foliage, and moderately vigorous, semi-upright growth habit. The new cultivar was discovered and selected as a single flowering plant within the progeny of the above stated cross-pollination during July 2018 in a controlled environment in Elburn, Ill.

Asexual reproduction of the new cultivar by in vitro shoot propagation since July 2018 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsompred' as a new and distinct cultivar of *Echinacea* plant:

1. Single-type, bright red-colored inflorescences;
2. Dark green-colored foliage; and
3. Moderately vigorous, compact-upright growth habit.

Plants of the new cultivar differ from plants of the female parent primarily in having brighter red-colored inflorescences, more main stems per plant, and a more compact growth habit. Plants of the new cultivar differ from plants of male parent primarily in having bright red-colored inflorescences that is different from the orange-colored inflorescences of the male parent and in having a more compact-upright growth habit.

Of the many commercially available *Echinacea* cultivars, the most similar in comparison to the new cultivar is SOMBRERO Hot Coral 'Balsomcor', U.S. Plant Pat. No. 23,097. However, in side-by-side comparisons, plants of the new cultivar differ from plants of 'Balsomcor' in at least the following characteristics:

1. Plants of the new cultivar have a red ray floret color that is different from the red-orange ray floret color of plants of 'Balsomcor'; and
2. Plants of the new cultivar have darker greyed-red and greyed-orange colored receptacle spines than plants of 'Balsomcor'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs may differ slightly from the color values cited in the detailed description, which accurately describes the colors of 'Balsompred'. The plants were approximately six months old. The plants were grown in one-gallon containers at three plants per pot for approximately 2.5 months in an outdoor nursery in Elburn, Ill.

DETAILED BOTANICAL DESCRIPTION

Figure 1:
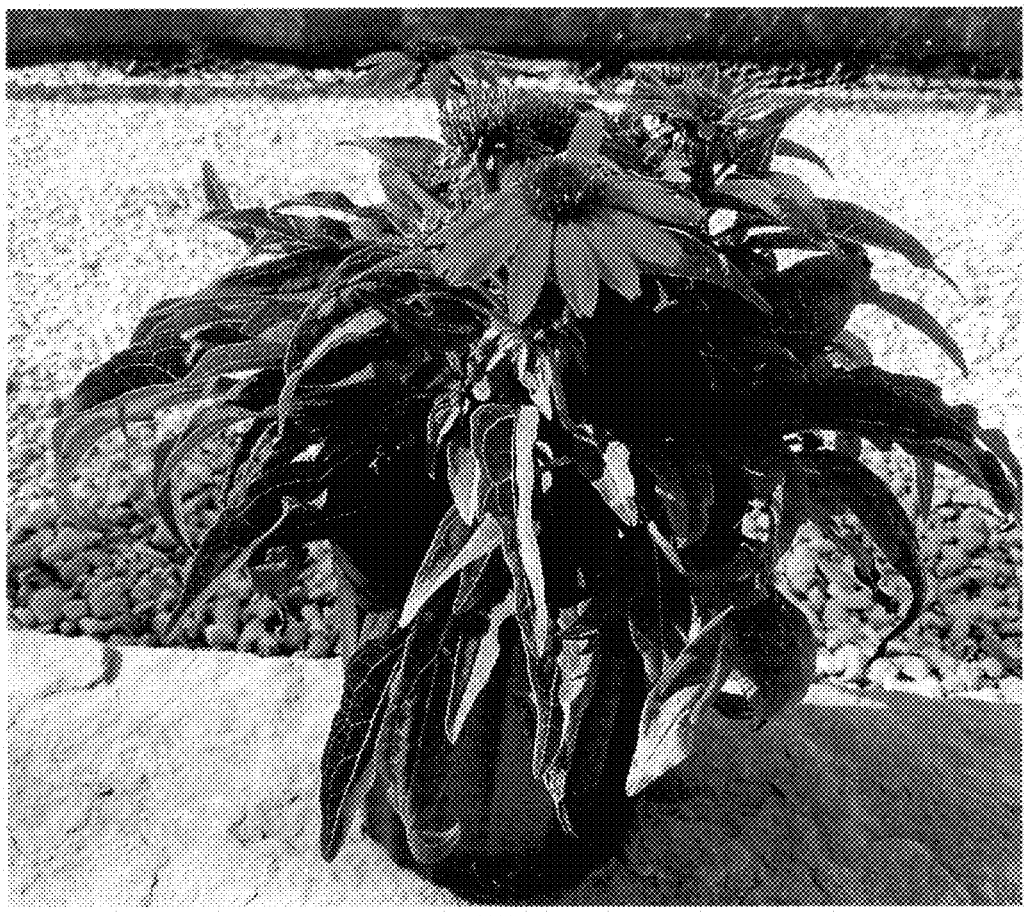
FIG. 1 illustrates a side view of the overall growth and flowering habit of 'Balsompred'.
Figure 2:
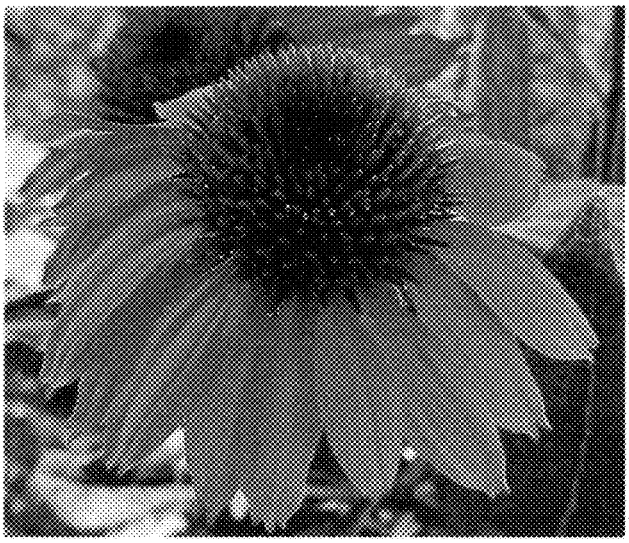
FIG. 2 illustrates a close-up view of an individual inflorescence of 'Balsompred'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2022 under natural light conditions in Naperville, Ill.

The following descriptions and measurements describe approximately six-month old plants produced from in vitro plantlets and grown under conditions comparable to those used in commercial practice. Approximately ten weeks after transfer to a greenhouse, plantlets were transplanted into one-gallon containers at three plants per pot utilizing a soilless growth medium and grown for four weeks. Plants were then transferred to an outdoor nursery environment in Elburn, Ill. and grown for approximately 2.5 months. Prior to transplant plants were grown in liners in a polycarbonate greenhouse in West Chicago, Ill. Greenhouse temperatures were maintained at approximately 70° F. to 75° F. (21.1° C. to 23.9° C.) during the day and approximately 60° F. to 65° F. (15.6° C. to 18.3° C.) during the night. Supplemental lighting was used. Measurements and numerical values represent averages of typical plants.

Botanical classification: *Echinacea* x *hybrida* 'Balsompred'.

Parentage:

*Female parent*.—Proprietary *Echinacea* x *hybrida* breeding selection coded E101-4-10-C, not patented.

*Male parent*.—Proprietary *Echinacea* x *hybrida* breeding selection coded E68-7-3-3-2, not patented.

Propagation:

*Type*.—In vitro propagation is preferred, divisions are possible.

*Time to initiate roots in vitro*.—Approximately 30 days at 18° C.

*Time to produce a rooted plantlet in summer*.—Approximately 30 days at 18° C.

*Root description*.—Fine, fibrous; grey to light brown in color.

*Rooting habit*.—Moderate density, moderate branching.

Plant description:

*Commercial crop time*.—Approximately 10 to 12 weeks from a rooted tissue culture plantlet to finish in a 15 cm container.

*Growth habit and general appearance*.—Herbaceous perennial, moderately vigorous, compact-upright.

*Hardiness*.—USDA Zone 4b (−25° F. to −20° F./−32° C. to −29° C.).

*Size*.—Height from soil level to top of plant plane: Approximately 24.0 cm. Width: Approximately 43.0 cm.

*Branching habit*.—No lateral branching, flowering stems grow from base. Quantity of main stems per plant: Approximately 3.

*Stems*.—Strength: Very strong. Aspect: Nearly erect. Shape: Rounded. Length to base of inflorescence: Approximately 17.0 cm. Diameter: Approximately 4.0 mm to 7.0 mm. Length of central internode: Approximately 3.2 cm. Texture: Densely pubescent with short strigose hairs. Color of young and mature stems: 146B to 146C with an overlay of 187A.

Foliage description:

*General description*.—Form: Simple. Arrangement: Alternate.

*Leaves*.—Aspect: Perpendicular to stem, subtending with age. Shape: Narrowly ovate to lanceolate. Margin: Entire, slightly undulate. Apex: Acute. Base: Attenuate. Venation pattern: Pinnate. Length of mature leaf: Approximately 14.5 cm to 18.0 cm. Width of mature leaf: Approximately 4.0 cm to 6.0 cm. Texture of upper surface: Dull, sparsely pubescent with short strigose hairs. Texture of lower surface: Moderately pubescent with short strigose hairs. Color of upper surface of young and mature foliage: Closest to NN137A with venation of 145C with midvein having an overlay of 187A at base. Color of lower surface of young and mature foliage: Closest to 147B with venation of 145C.

*Petiole*.—Shape: V-shaped. Length: Approximately 13.0 cm to 18.0 cm. Diameter: Approximately 3.0 mm to 5.0 mm. Texture of upper surface: Glabrous. Texture of lower surface: Sparsely covered with very short strigose hairs. Color of upper and lower surfaces: 145B to 145C, with upper surface having an overlay of 187A.

Flowering description:

*Flowering habit*.—'Balsompred' is freely flowering blooming from late spring through late summer under outdoor growing conditions.

*Lastingness of individual inflorescence on the plant*.—Approximately 3 weeks.

Inflorescence description:

*General description*.—Type: Solitary, composite. Persistent. Shape: Conical. Aspect: Facing upward. Arrangement: Terminal, held upright on strong peduncles. Fragrance: Faintly sweet. Quantity per plant: Approximately 5. Height: Approximately 3.0 cm. Diameter: Approximately 8.0 cm.

*Peduncle*.—Strength: Strong. Aspect: Erect to approximately 45° from vertical. Length: Approximately 8.0 cm. Diameter: Approximately 3.0 mm to 5.0 mm. Texture: Moderately pubescent with short strigose hairs. Color: 146B to 146C with an overlay of 187A.

*Bud*.—Quantity per plant: Approximately 10. Shape: Flattened globular with immature ray florets nearly erect. Length: Approximately 1.5 cm. Diameter: Approximately 2.0 cm. Color: Outer ray florets of 187B with bud center of 187A.

*Ray florets*.—Quantity per inflorescence: Approximately 18. Arrangement: In a single whorl, slightly imbricate. Aspect: Perpendicular to disc, subtending with age. Shape: Elliptic. Appearance: Matte. Margin: Entire. Apex: Three acute tips. Base: Attenuate. Length: Approximately 3.5 cm. Width: Approximately 1.1 cm. Texture of upper surface: Glabrous, ribbed longitudinally. Texture of lower surface: Sparsely pubescent, ribbed longitudinally. Color of upper surface when first open: Closest to 45A blended with N45A. Color of lower surface when first open: 186A to 186B with 70A. Color of upper surface when fully open: Closest to 45A, with senescence fades to closest to 185A to 185B. Color of lower surface when fully open: 186A to 186B.

*Disc florets*.—Disc diameter: Approximately 3.5 cm. Quantity per inflorescence: Approximately 270. Arrangement: Spirally arranged in center of inflorescence. Shape: Tubular. Margin of free portion: Entire. Apex: Five acute tips. Base: Fused into a tube. Length: Approximately 1.1 cm. Diameter: Approximately 2.0 mm. Texture: Glabrous. Color of upper or inner surface when first and fully open: 146D with 187A at tips. Color of lower or outer surface when first and fully open: 146D with 187A at tips and base of NN155D.

*Receptacle*.—Shape: Conical. Height: Approximately 1.2 cm. Diameter: Approximately 1.5 cm. Color: 155D.

*Phyllaries*.—Quantity per inflorescence Approximately 35. Arrangement: In multiple whorls. Appearance: Dull, stiff. Shape: Narrowly ovate to lanceolate, strongly curved towards the peduncle. Margin: Entire, ciliate. Apex: Acute. Base: Truncate. Length: Approximately 1.1 cm to 1.5 cm. Width: Approximately 2.0 mm to 4.0 mm. Texture of upper or inner surface: Glabrous. Texture of lower or outer surface: Sparsely pubescent with short strigose hairs. Color of upper surface: 137A, innermost with an overlay of 187A. Color of lower surface: 137B, innermost with an overlay of 187A.

*Receptacle spines*.—Number of spines per disc: Approximately 270. Shape: Acicular. Length: Approximately 1.4 cm. Width at widest point: Approximately 2.0 mm. Apex: Acute. Base: Truncate. Texture: Glabrous. Color: Apex 187A with 167B nearest mid-section, mid-section of 146D, and base of NN155D.

*Reproductive organs*.—Androecium: Present on disc florets only. Stamen quantity: 5 per floret. Anther shape: Oblong, basifixed. Anther length: Approximately 3.0 mm. Anther color: Closest to 199A. Filament length: Approximately 2.0 mm. Filament color: 155D. Pollen amount: Abundant. Pollen color: 17A. Gynoecium: Present on disc florets only. Pistil quantity: 1 per floret. Pistil length: Approximately 1.1 cm. Stigma shape: Bifid. Stigma length: Approximately 2.0 mm. Stigma color: 187A with N187A. Style length: Approximately 7.0 mm. Style color: 145D with 155D with an overlay of 187A nearest stigma. Ovary length: Approximately 3.0 mm. Ovary color: NN155D.

Seed and fruit production: Neither seed nor fruit production has been observed.

Disease and pest resistance: Resistance to pathogens and pests common to *Echinacea* has not been observed.

What is claimed is:

1. A new and distinct cultivar of *Echinacea* plant named 'Balsompred', substantially as herein illustrated and described.

* * * * *